US008480738B2

(12) United States Patent
 Edie et al.

(10) Patent No.: US 8,480,738 B2
(45) Date of Patent: Jul. 9, 2013

(54) IMPLANT WITH NESTED MEMBERS AND METHODS OF USE

(75) Inventors: Jason A. Edie, Salt Lake City, UT (US); Lloyd Guyton Bowers Cooper, Birmingham, AL (US); Jerrod Bradley Windham, Auburn, AL (US); John Caleb Dawson, Chicago, IL (US); Don Byron Walker, II, Muscle Shoals, AL (US); Barry K. Patterson, North Charleston, SC (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 567 days.

(21) Appl. No.: 12/756,413

(22) Filed: Apr. 8, 2010

(65) Prior Publication Data

US 2010/0198352 A1 Aug. 5, 2010

Related U.S. Application Data

(63) Continuation of application No. 11/491,379, filed on Jul. 21, 2006, now Pat. No. 7,731,752.

(51) Int. Cl.
 *A61F 2/44* (2006.01)
(52) U.S. Cl.
 USPC ...................................................... 623/17.11
(58) Field of Classification Search
 USPC ............................... 623/17.11–17.16; 606/90
 See application file for complete search history.

(56) References Cited

U.S. PATENT DOCUMENTS

| 3,898,999 | A | * | 8/1975 | Haller | 137/512.1 |
|---|---|---|---|---|---|
| 4,309,777 | A | * | 1/1982 | Patil | 623/17.13 |
| 4,401,112 | A | * | 8/1983 | Rezaian | 606/279 |
| 4,657,550 | A | * | 4/1987 | Daher | 623/17.11 |
| 5,192,327 | A | * | 3/1993 | Brantigan | 623/17.11 |
| 5,236,460 | A | * | 8/1993 | Barber | 623/17.15 |
| 5,290,312 | A | * | 3/1994 | Kojimoto et al. | 623/17.15 |
| 5,375,823 | A | * | 12/1994 | Navas | 623/17.15 |
| 5,405,391 | A | * | 4/1995 | Hednerson et al. | 623/17.15 |
| 5,458,641 | A | * | 10/1995 | Ramirez Jimenez | 623/17.11 |
| 5,702,455 | A | * | 12/1997 | Saggar | 623/17.15 |
| 6,176,881 | B1 | * | 1/2001 | Schar et al. | 623/17.11 |
| 6,193,756 | B1 | * | 2/2001 | Studer et al. | 623/17.15 |
| 6,375,683 | B1 | * | 4/2002 | Crozet et al. | 623/17.15 |
| 6,419,705 | B1 | * | 7/2002 | Erickson | 623/17.16 |
| 6,454,806 | B1 | * | 9/2002 | Cohen et al. | 623/17.15 |
| 6,524,341 | B2 | * | 2/2003 | Lang et al. | 623/17.15 |
| 6,981,989 | B1 | * | 1/2006 | Fleischmann et al. | 623/17.11 |
| 7,235,102 | B2 | * | 6/2007 | Ferree et al. | 623/17.12 |
| 8,152,852 | B2 | * | 4/2012 | Biyani | 623/17.16 |
| 2002/0128716 | A1 | * | 9/2002 | Cohen et al. | 623/17.15 |
| 2003/0004575 | A1 | * | 1/2003 | Erickson | 623/17.15 |
| 2003/0109932 | A1 | * | 6/2003 | Keynan | 623/23.18 |
| 2003/0199980 | A1 | * | 10/2003 | Siedler | 623/17.11 |
| 2004/0024460 | A1 | * | 2/2004 | Ferree | 623/17.12 |
| 2004/0024461 | A1 | * | 2/2004 | Ferree | 623/17.13 |
| 2004/0127991 | A1 | * | 7/2004 | Ferree | 623/17.11 |
| 2004/0243238 | A1 | * | 12/2004 | Arnin et al. | 623/17.12 |

(Continued)

*Primary Examiner* — Mary Hoffman

(57) ABSTRACT

Vertebral implants that may be movable between collapsed and expanded orientations to space apart first and second vertebral members. The implants may include first and second contact surfaces to contact against the vertebral members. The implants may include nested struts. The implants may have a first height measured between the contact surfaces in the collapsed orientation with a first amount of overlap in the struts. The implants may have a second height in the expanded orientation with a lesser amount of overlap in the struts.

20 Claims, 4 Drawing Sheets

U.S. PATENT DOCUMENTS

| | | | |
|---|---|---|---|
| 2004/0260396 A1* | 12/2004 | Ferree et al. | 623/17.12 |
| 2005/0015152 A1* | 1/2005 | Sweeney | 623/17.14 |
| 2005/0085910 A1* | 4/2005 | Sweeney | 623/17.11 |
| 2005/0096744 A1* | 5/2005 | Trieu et al. | 623/17.11 |
| 2005/0107877 A1* | 5/2005 | Blain | 623/16.11 |
| 2005/0154459 A1* | 7/2005 | Wolek et al. | 623/17.11 |
| 2005/0187634 A1* | 8/2005 | Berry | 623/17.15 |
| 2006/0074490 A1* | 4/2006 | Sweeney | 623/17.15 |
| 2006/0100710 A1* | 5/2006 | Gutlin et al. | 623/17.15 |
| 2006/0116767 A1* | 6/2006 | Magerl et al. | 623/17.12 |
| 2007/0118225 A1* | 5/2007 | Hestad et al. | 623/17.16 |
| 2007/0173940 A1* | 7/2007 | Hestad et al. | 623/17.12 |
| 2007/0233254 A1* | 10/2007 | Grotz et al. | 623/17.11 |
| 2008/0161933 A1* | 7/2008 | Grotz et al. | 623/17.16 |
| 2008/0288073 A1* | 11/2008 | Renganath et al. | 623/17.12 |
| 2009/0204215 A1* | 8/2009 | McClintock et al. | 623/17.11 |

* cited by examiner

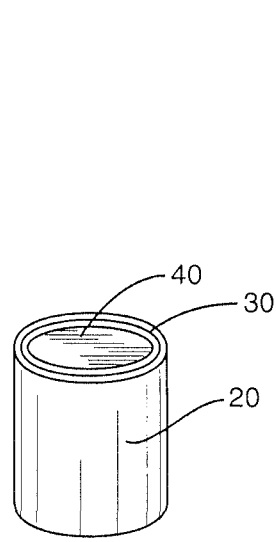
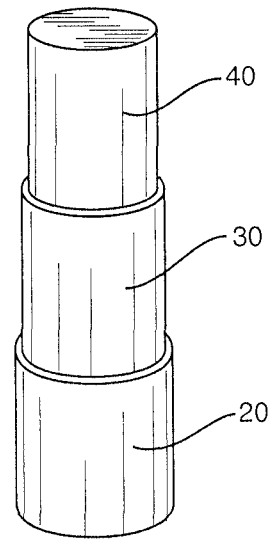
FIG. 7A  FIG. 7B
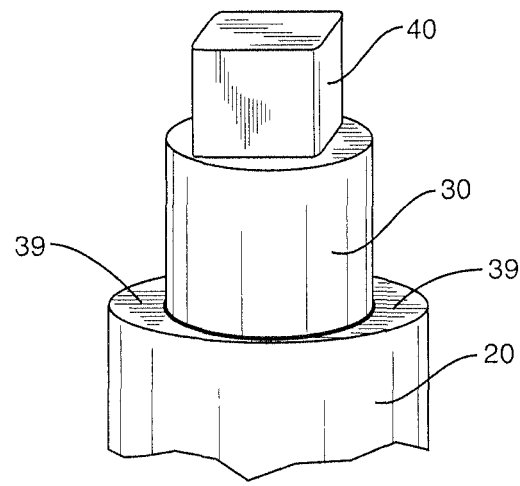
FIG. 8

IMPLANT WITH NESTED MEMBERS AND METHODS OF USE

RELATED APPLICATION

The present application is a continuation application of U.S. patent application Ser. No. 11/491,379, filed on Jul. 21, 2006, herein incorporated by reference in its entirety.

BACKGROUND

The present application is directed to vertebral implants and methods of use, and more particularly, to implants that are adjustable between a first reduced size to ease insertion into the patient, and a second enlarged size to space vertebral members.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

The implants may be adjustable between a first, reduced size that facilitates insertion into the patient in a minimally invasive manner. Once inserted, the implant may be expanded to a larger second size.

SUMMARY

The application is directed to implants and methods of use for positioning between vertebral members. The implants may be movable between collapsed and expanded orientations to space apart first and second vertebral members. The implants may include first and second contact surfaces to contact against the vertebral members. The implants may include nested struts. The implants may have a first height measured between the contact surfaces in the collapsed orientation with a first amount of overlap in the struts. The implants may have a second height in the expanded orientation with a lesser amount of overlap in the struts.

BRIEF DESCRIPTION OF THE DRAWINGS

FIGS. 7A-7B are perspective views of an implant moving from a collapsed orientation to an expanded orientation according to one embodiment.

FIG. 8 is a perspective view of an implant according to one embodiment.

DETAILED DESCRIPTION

The application is directed to implants that are adjustable between collapsed and expanded orientations. The collapsed orientation includes a smaller height to facilitate insertion into the patient. The expanded orientation includes a larger height for spacing and/or supporting the vertebral members. The implants generally include three or more members that are nested together in the collapsed orientation. The members may move outward away from each other in the expanded orientation. An expansion means may be operatively connected to one or more of the sections to move the implants between the orientations.

Figure 1:
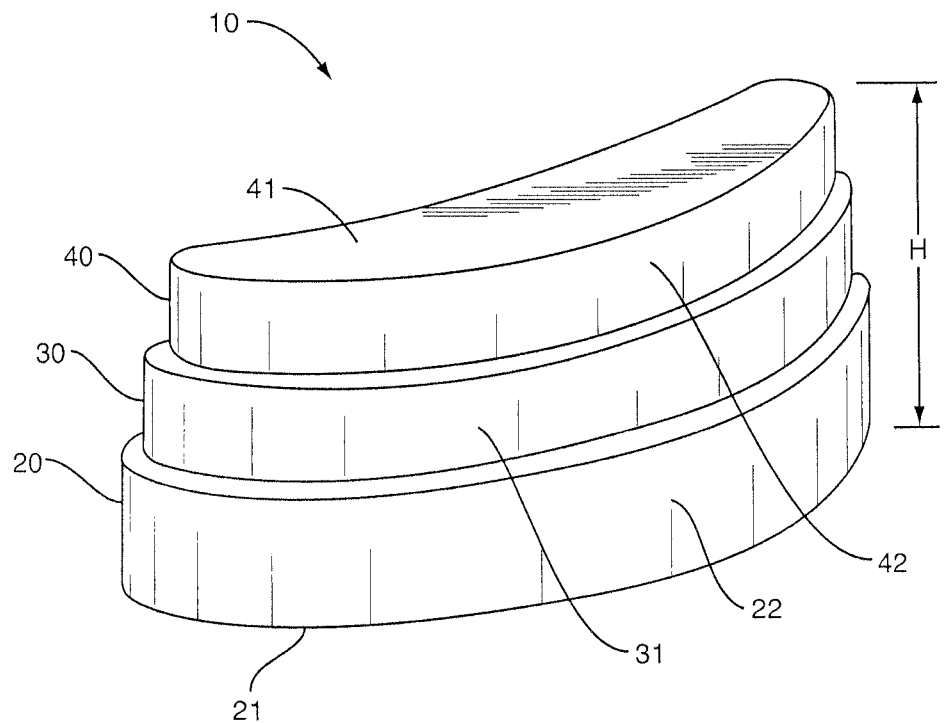
FIG. 1 is a perspective view of an implant in an expanded orientation according to one embodiment.

FIG. 1 illustrates an implant 10 in the expanded orientation with a height H. The implant 10 includes a first member 20, second member 30, and a third member 40 that are in a telescoping arrangement. The second member 30 extends outward from the first member 20, and the third member 40 extends outward from the second member 30. The first member 20 includes a contact surface 21 that contacts a first vertebral member, and the third member 40 includes contact surface 41 that contacts a second vertebral member. The contact surfaces 21, 41 may be textured to grip the vertebral body. For example, teeth, ridges, or grooves can be formed to improve gripping capability.

Figure 2:
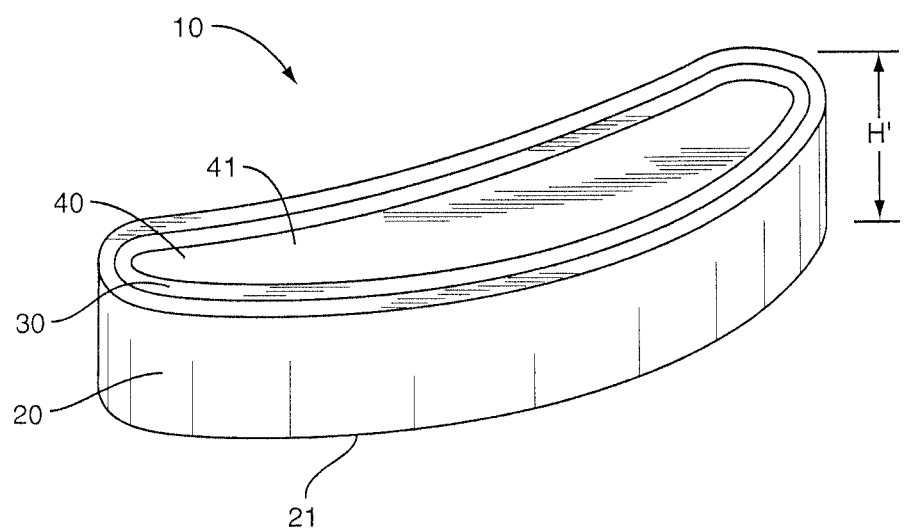
FIG. 2 is a perspective view of an implant in a collapsed orientation according to one embodiment.

FIG. 2 illustrates the implant 10 in a collapsed orientation. The members 20, 30, 40 are nested together with an overall height H' that is less than the height H. The first member 20 is sized to receive the second member 30, which itself is sized to receive the third member 40. The collapsed orientation allows for insertion of the implant 10 into the patient in a minimally-invasive manner. Once the implant 10 is inserted, the height can be increased as necessary. The implant 10 may be used within the patient at a variety of different heights that range between height H and height H'.

Figure 3:
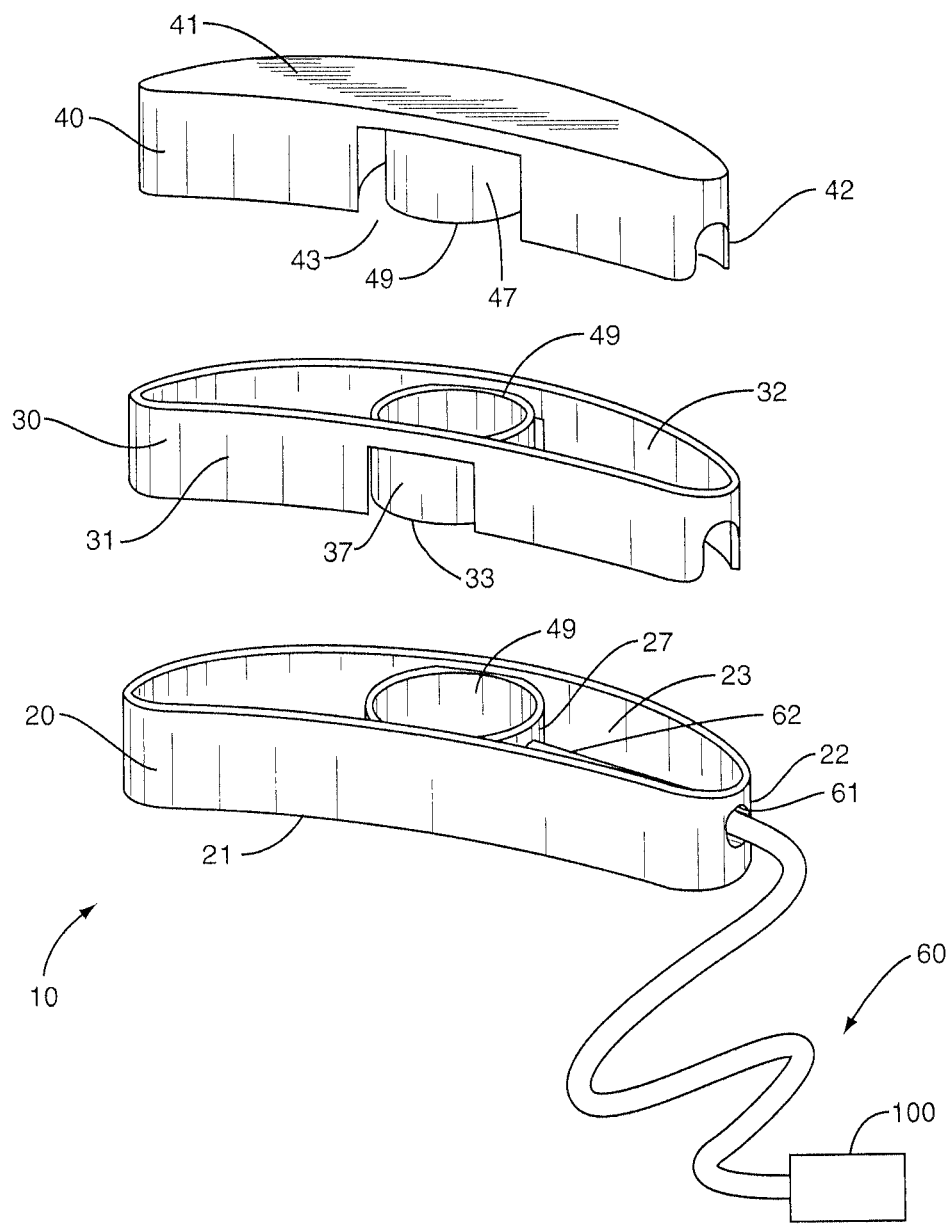
FIG. 3 is an exploded perspective view of an implant according to one embodiment.

FIG. 3 illustrates an exploded view of the implant 10 that includes first, second, and third members 20, 30, 40. The first member 20 includes sidewalls 22 that extend outward from the contact surface 21. The sidewalls 22 and contact surface 21 form an interior space 23 that is sized to receive the other members 30, 40.

The second member 30 includes a sidewall 31 with a shape and size that corresponds to the first member 20. An interior space 32 is formed within the sidewalls and is sized to fit within the interior space 23 of the first member 20. The third member 40 includes a contact surface 41 and an outwardly-extending sidewall 42. The shape and size of the sidewall 42 corresponds to the second member 30 and is sized to fit within the interior space 32 of the second member 30. In some embodiments, one or more of the sidewalls 22, 31, 42 contact during the movement between the collapsed and expanded orientations. The surfaces of the sidewalls 22, 31, 42 may be substantially smooth to facilitate the sliding movement. Alternatively, the members 20, 30, 40 may be sized such that the sidewalls 22, 31, 42 do not touch.

As illustrated in FIG. 1, the members 20, 30, 40 are in an overlapping configuration in the expanded orientation. The amount of overlap may vary depending upon the overall height of the implant 10. In a reduced height that is only slightly greater than the collapsed height H', the amount of overlap is large. In the expanded height H, the amount of overlap is small. In one embodiment, the sidewalls 22, 31, 42 overlap forming a three-ply arrangement when the implant 10 is in the collapsed orientation. In the expanded orientation, the amount of overlap is less with a two-ply arrangement between sidewalls 22, 31, and sidewalls 31, 42. The amount of overlap of the sidewalls 22, 31, 42 may vary between members 20, 30, 40. By way of example, the amount of overlap between sidewall 22 and 31 may be a first amount, with the overlap between sidewall 31 and 42 being a second, different amount. The overlap gives torsional support to the implant 10 and prevents the members 20, 30, 40 from separating during the application of twisting force applied about an axis that extends vertically through the implant 10.

Figure 4:
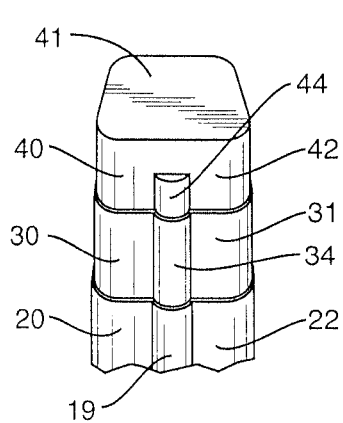
FIG. 4 is a partial perspective view of an implant in an expanded orientation according to one embodiment.

As illustrated in FIG. 4, one or more of the members 20, 30, 40 may further include a rib 44. In this embodiment, third member 40 includes a rib 44 that extends outward from the sidewall 42. Second member 30 includes a receiver 34 sized to receive the rib 44. The rib 44 moves within the receiver 34 during movement of the implant 10 between the collapsed and expanded orientations. Rib 44 and receiver 34 maintain the alignment between the second and third members 30, 40. Likewise, rib 34 of the second member 30 fits within receiver 19 on the first member 20. FIG. 4 illustrates a single rib 44 and receiver 34 pair. Multiple ribs and receivers may be positioned along the various members 20, 30, 40 as necessary to maintain the alignment.

The height of the sidewalls 22, 31, 42 may be the same or different. In one embodiment, sidewall 22 of the first member 20 is greater than the other sidewalls 31, 42. This causes the second and third members 30, 40 to completely nest within the first member 20 in the collapsed orientation. The sidewalls 22, 31, 42 may further include substantially the same heights.

Figure 5:
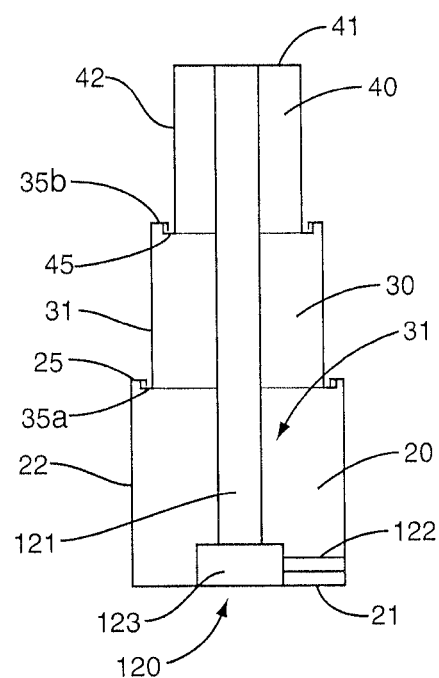
FIG. 5 is a schematic view of an implant according to one embodiment.

As illustrated in FIG. 5, the members 20, 30, 40 may further include flanges 25, 35, 45. The flanges 25, 35, 45 extend from the sidewalls 22, 31, 42 and contact together to control an extent of expansion and prevent overextension of one or more of the members 20, 30, 40. The flanges 25, 35, 45 may extend around the entire periphery or a limited section of each member 20, 30, 40. In the embodiment of FIG. 5, flanges 35a, 45 are positioned at the bottom of members 30, 40, with flanges 25, 35b positioned at the top of members 20, 30. The flanges 25, 35, 45 may also be positioned at other locations along the members 20, 30, 40 depending upon the amount of desired expansion of the implant 10, and amount of sidewall overlap.

In some embodiments as illustrated in FIG. 4, the sidewalls 22, 31, 42 are substantially continuous and extend around the entire periphery of the member 20, 30, 40. In other embodiments as illustrated in FIG. 3, one or more of the sidewalls 31, 42 include gaps 33, 43. Gaps 33, 43 may be positioned at various points about the sidewalls and may have a variety of shapes and sizes.

Members 20, 30, 40 may further include struts 27, 37, 47 within the sidewalls 22, 31, 42 as illustrated in FIG. 3. Each of the struts 27, 37, 47 is formed by an outer wall that forms an enclosed chamber 49. The chamber 49 is sized to fit within the interior space formed by the sidewalls. The struts 27, 37, 47 include a telescoping configuration that nest together in the collapsed orientation. In the embodiment of FIG. 3, the strut 27 of the first member 20 is the largest, with the struts 37, 47 being smaller to fit inside within in the collapsed orientation. In the embodiment of FIG. 3, the struts 27, 37, 47 are substantially circular, although other embodiments may include different shapes. FIG. 3 illustrates an embodiment with each member 20, 30, 40 including a single strut. In other embodiments, each member 20, 30, 40 may include two or more struts.

An expansion means may be operatively connected with the interior space to move the implant 10 between the expanded and collapsed orientations. In one embodiment as illustrated in FIG. 3, a port 61 extends through the sidewall 22 of the first member 20 and leads into the chamber 49 formed within the strut 27. A conduit 62 may further lead from the port 61 into the strut 27. Alternatively, the port 61 may be positioned through the sidewall 22 and strut 27 and directly into chamber 49. The port 61 provides for introducing fluid into the chamber 49 that is moved by pump 100. A valve (not illustrated) is disposed in the port 61 that allows introduction of fluid into the chamber 49 and prevents fluid from exiting. A variety of fluids may be introduced into the chamber 49, including saline, water, and air. One example of an expansion means is disclosed in U.S. patent application Ser. No. 11/412, 671 filed on Apr. 27, 2006 and titled Expandable Intervertebral Spacers and Methods of Use. This Application is assigned to Medtronic Sofamor Danek and is herein incorporated by reference in its entirety.

In use, the implant 10 is placed in the collapsed orientation and inserted into the patient. Once positioned within the patient, the pump 100 moves fluid through the port 61 and into the chamber 49. This causes the members 20, 30, 40 to begin moving outward towards the expanded orientation. The amount of expansion and speed of expansion are dependent on the amount of pressure of the fluid being introduced through the port 61. In one embodiment, the pump 100 is removed from the inlet 61 and the implant 10 may remain within the patient. The valve seals the fluid within the chamber 49 and prevents escape. In another embodiment, the pump 100 removes the fluid from the chamber 49 at a predetermined time. The removal of the fluid causes the members 20, 30, 40 to move towards the collapsed orientation. Once the fluid is removed, the implant 10 may be removed from the patient.

The expansion means may further include a jack mechanism 120 as illustrated in FIG. 5. The device 120 may include a telescoping arm 121 that is positioned between the contact surfaces 21, 41. A gear 123 may be operatively connected to the arm 121, with a rotational input 122 leading from the sidewall 22 to the gear 123. Rotation of the gear 123 via the input 122 causes the arm 121 to expand and contract. This movement causes the implant 10 to move between the expanded and collapsed orientations. In one embodiment, arm 121 is constructed of telescoping members. The members telescope together in an overlapping arrangement in the collapsed position. One example of a jack mechanism is disclosed in U.S. patent application Ser. No. 11/415,042 filed on May 1, 2006 and titled Expandable Intervertebral Spacers and Methods of Use. This Application is assigned to Medtronic Sofamor Danek and is herein incorporated by reference in its entirety.

Use of the implant 10 with a jack mechanism 120 is similar to the fluid embodiment described above. The implant 10 is inserted into the patient while in the collapsed orientation. Once inserted, the surgeon accesses the rotational input 122 to apply a rotational force to the gear 123. This causes the arm 121 to expand and move the implant 10 towards the expanded orientation. The implant 10 may either remain within the patient in the expanded orientation, or may be moved back to the collapsed orientation for removal.

In the embodiment of FIG. 1, the implant 10 includes three members 20, 30, 40. The implant 10 may also include more than three members. FIGS. 6A-6D illustrate an embodiment with four separate members 20. Other embodiments may feature more than four members as necessary. The size and shape of the members may also vary depending upon the embodiment. FIG. 1 illustrates an embodiment with an oval or kidney shape. FIG. 4 illustrates an embodiment with a rectangular shape, FIGS. 6A-6D illustrate a triangular shape, and FIGS. 7A-7B illustrate a circular shape. In some embodiments, the different members may include different shapes. FIG. 8 includes a first member 20 that is substantially oval shape, a second member 30 that is substantially circular, and a third member 40 that is substantially rectangular. The members 20, 30, 40 are sized to nest together in the collapsed orientation. One or more shelves 39 may extend across a member 20 to enclose the interior space. Shelves 39 are particularly useful when the nested member is either considerably smaller than the receiving member, or includes a different shape.

Figure 6A:
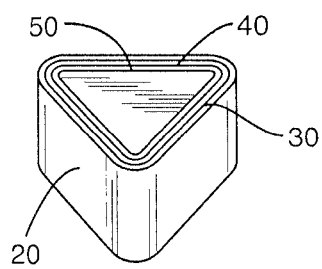
FIGS. 6A-6D are perspective views of an implant moving from a collapsed orientation to an expanded orientation according to one embodiment.
Figure 6B:
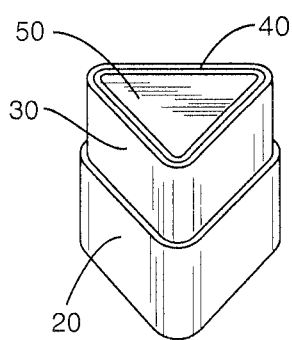
Figure 6C:
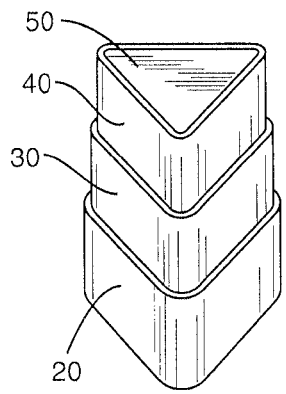
Figure 6D:
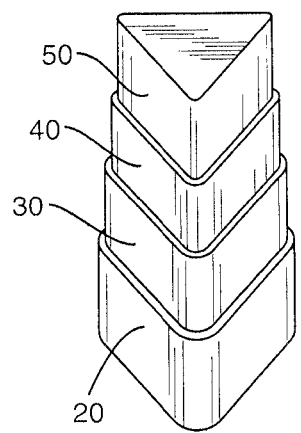

In some embodiments, deployment of the implant 10 from the collapsed orientation comprises different order of movement of each of the members. FIGS. 7A and 7B illustrate an embodiment with the members 20 nested together as illustrated in FIG. 7A. Movement towards the expanded orientation causes each of the members 20, 30, 40 to move outward as illustrated in FIG. 7B. Each member 20, 30, 40 may move the same amount, or some members may move a greater amount. In another embodiment, the members 20 move in an ordered sequence as illustrated in FIGS. 6A-6D. A first amount of movement from the collapsed orientation of FIG. 6A to a partially expanded orientation of FIG. 6B comprises movement between the first and second members 20, 30. Members 40 and 50 remain within the second member 30. Continued movement as illustrated in FIG. 6C causes movement between the second member 30 and the third member 40. The fourth member 50 remains stationary relative to the third member 40. Continued movement as illustrated in FIG. 6D finally results in fourth member 50 moving relative to the third member 40.

The contact surfaces 21, 41 may include a variety of shapes and orientations. In one embodiment as illustrated in FIG. 1, surfaces 21, 41 are substantially parallel. In other embodiments, surfaces 21, 41 may be positioned at an angle to conform to the curvature of the spine including the cervical, thoracic, and lumbosacral curves. In one embodiment, wedge-shaped inserts may be attached to the surfaces 21 and/or 41 to address the curves of the spine.

The implant 10 may be inserted into the patient from a variety of approach angles. One embodiment includes access via an anterior approach to the cervical spine. Other applications contemplate other approaches, including posterior, postero-lateral, antero-lateral and lateral approaches to the spine, and accessing other regions of the spine, including the cervical, thoracic, lumbar and/or sacral portions of the spine.

FIG. 3 includes an embodiment with fluid introduced into the chamber 49. In another embodiment (not illustrated), the members 20, 30, 40 mate together to form an enlarged, enclosed interior space to receive the fluid. The fluid is moved into and out of the interior space to control the height of the device 10. The difference with this embodiment is the larger area for receiving the fluid and providing the expansion force to the members 20, 30, 40. As with the other embodiment, the amount of expansion and speed of expansion are dependent on the amount of pressure of the fluid being introduced through the port 61.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. An implant movable between collapsed and expanded orientations to space apart first and second vertebral members, the implant comprising:
   a first contact surface to contact against the first vertebral member;
   a second contact surface to contact against the second vertebral member;
   an outer wall extending between the first and second contact surfaces and comprising a plurality of separate outer wall sections positioned in a nested arrangement;
   at least one strut formed within each outer wall section, each of the at least one strut is at least partially separated from the outer wall and the at least one strut has a telescoping configuration such that the struts are configured to move between extended arrangement and in a nested arrangement; and
   an enclosed inner chamber positioned within the outer wall and formed by each of the struts positioned in the nested arrangement;
   in the collapsed orientation, the implant having a first height measured between the contact surfaces and having a greater amount of overlap in the plurality of separate outer wall sections and a greater amount of overlap of the struts;
   in the expanded orientation, the implant having a greater second height measured between the contact surfaces and having a lesser amount of overlap in the plurality of separate outer wall sections and a lesser amount of overlap of the struts; the enclosed inner chamber being sealed to contain the fluid in both the collapsed and expanded orientations.

2. The implant of claim 1, wherein the inner chamber extends between the first and second contact surfaces.

3. The implant of claim 1, wherein undersides of the first and second contact surfaces form portions of the inner chamber.

4. The implant of claim 1, wherein the inner chamber is spaced at least partially away from the outer wall.

5. The implant of claim 1, wherein the outer wall includes a triple ply in the collapsed orientation.

6. The implant of claim 1, further comprising a conduit that extends through a port in the outer wall and into the inner chamber.

7. The implant of claim 1, wherein the outer wall includes a non-circular shape to prevent rotation of the outer wall sections when the implant moves between the collapsed and expanded orientations.

8. An implant movable between collapsed and expanded orientations to space apart first and second vertebral members, the implant comprising:
- a first contact surface to contact against the first vertebral member;
- a second contact surface to contact against the second vertebral member;
- an outer wall extending between the first and second contact surfaces;
- an enclosed chamber positioned within the outer wall and formed by a plurality of nested struts, each of the plurality of nested struts being at least partially separated from the outer wall sections such that have telescoping configuration such that the struts are configured to move between extended arrangement and in a nested arrangement;
- an interior space formed between the outer wall and the inner chamber;
- the implant having a first height measured between the contact surfaces in the collapsed orientation with a first amount of overlap in the plurality of struts and a second height in the expanded orientation with a lesser amount of overlap in the plurality of separate struts.

9. The implant of claim 8, wherein the enclosed chamber is sealed to contain a substance in the expanded orientation.

10. The implant of claim 9, wherein the enclosed chamber is sealed to contain a substance in the collapsed orientation.

11. The implant of claim 8, wherein the outer wall includes a plurality of separate outer wall sections positioned in a nested arrangement.

12. The implant of claim 11, wherein a first one of the outer wall sections extends outward from the first contact surface and a second one of the outer wall sections extends outward from the second contact surface.

13. The implant of claim 8, wherein the interior space is divided into a first section on a first side of the enclosed chamber and a second section on a second side of the enclosed chamber.

14. The implant of claim 8, wherein the interior space is enclosed within the outer wall.

15. An implant movable between collapsed and expanded orientations to space apart first and second vertebral members, the implant comprising:
- a first member with a first contact surface to contact against the first vertebral member, a first outer sidewall, and a first interior strut being at least partially spaced away from the first outer sidewall;
- a second member with a second contact surface to contact against the second vertebral member, a second outer sidewall, and a second interior strut being at least partially spaced away from the second outer sidewall;
- an intermediate member including a third outer sidewall and a third strut being at least partially spaced away from the third outer sidewall;
- the members positioned together such that the struts are in a telescoping nested arrangement forming a sealed chamber, the members movable between the collapsed orientation having a first height measured between the contact surfaces and having a first amount of overlap in the struts and the expanded orientation with a greater second height and a lesser amount of overlap in the struts.

16. The implant of claim 15, wherein the intermediate member is nested together with the first and second outer sidewalls.

17. The implant of claim 15, wherein the members have non-circular shapes to prevent rotation as the members move between the collapsed and expanded orientations.

18. The implant of claim 15, further comprising a conduit that extends through one of the first and second outer sidewalls and into the chamber.

19. The implant of claim 15, further comprising an interior space positioned laterally between the struts and the first and second outer sidewalls and longitudinally between the first and second contact surfaces.

20. The implant of claim 19, wherein a first portion of the interior space is positioned laterally on opposing sides of the struts.

* * * * *